US005151410A

United States Patent [19]

Giersch et al.

[11] Patent Number: 5,151,410

[45] Date of Patent: Sep. 29, 1992

[54] USE OF A SPIRANIC COMPOUND AS A PERFUMING INGREDIENT

[75] Inventors: Wolfgang K. Giersch, Bernex; Pierre-Alain Blanc, Crassier; Karl-Heinrich Schulte-Elte, Onex, all of Switzerland

[73] Assignee: Firmenich S.A., Geneva, Switzerland

[21] Appl. No.: 832,205

[22] Filed: Feb. 6, 1992

[30] Foreign Application Priority Data

Mar. 15, 1991 [CH] Switzerland .......................... 796/91

[51] Int. Cl.[5] ................................................ A61K 7/46

[52] U.S. Cl. .................................. 512/9; 252/174.11; 252/8.6; 424/76.4

[58] Field of Search ............................ 512/9; 568/367; 424/76.4; 252/174.11

[56] References Cited

U.S. PATENT DOCUMENTS 4,261,866 4/1981 Barton et al. .......................... 512/9
4,448,712 5/1984 van der Weerdt ..................... 512/9

OTHER PUBLICATIONS

Kane et al., Org. Synth., vol. 61, pp. 129-133 (1983).
Zipkin et al., Synthesis, vol. 12, pp. 1035-1037 (1980).
Natale et al., Org. Prep. Proceed Int., vol. 9, pp. 108-108 (1977).
Kane, Synthesis Comm., vol. 6(3), pp. 237-242 (1976).

*Primary Examiner*—James H. Reamer
*Attorney, Agent, or Firm*—Pennie & Edmonds

[57] ABSTRACT

Spiro[5.7]tridec-1-ene-3-one is a useful perfuming ingredient for the preparation of perfuming bases and perfumed articles to which it imparts odor notes of the costus, animal and leather type.

5 Claims, No Drawings

USE OF A SPIRANIC COMPOUND AS A PERFUMING INGREDIENT

BRIEF SUMMARY OF THE INVENTION

The invention relates to a method to confer, improve, enhance or modify the odor properties of a perfuming composition or a perfumed article, which method comprises adding to said composition or article a fragrance effective amount of spiro[5.7]tridec-1-ene-3-one.

It is another object of the invention to provide a perfuming composition containing as an active perfuming ingredient spiro[5.7]tridec-1-ene-3-one in combination with current solvents, carriers or excipients as well as other perfuming ingredients of current use.

The invention further relates to a perfumed article containing as an active perfuming ingredient spiro[5.7]-tridec-1-ene-3-one.

A further object of the invention is a method to confer, improve, enhance or modify the odor properties of a perfuming composition or a perfumed article, which method comprises adding to a perfuming base or a consumer product spiro[5.7]tridec-1-ene-3-one in an olfactively perceptible amount.

BACKGROUND OF THE INVENTION

The present invention relates to the perfume industry and, in particular, it concerns the use in perfumery of sprio[5.7]tridec-1-ene-3-one of formula

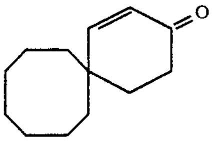

(I)

Spiro[5.7]-tridec-1-ene-3-one is a known chemical entity. Kane Vinayak has described its preparation starting from enamine derivatives of cycloaliphatic aldehydes by reacting with methyl vinyl ketone [Synth. Commun. 6, 237–42 (1976)]. An analogous synthesis has been proposed by N. R. Natale et al. [Org. Prep. Proced. Int. 9, 103–8 (1977)], while R. E. Ziplin et al. [Synthesis 1035–7 (1980)] have described a process which resorted to phenyl-selenium and oxygenated water. Finally, Kane Vinayak et al. have been able to prepare spiro-ketone (I) by condensation of cyclooctanecarboxaldehyde with piperidine, followed by a cyclisation with methyl vinyl ketone [Org. Synth. 61, 129–133 (1983)].

Used as an intermediate product for the preparation of cyclophane derivatives, spiro[5.7]tridec-1-ene-3-one has not been recognized in the prior art as having potential useful odor properties. In effect, none of the cited documents mentions nor suggests the possibility of using this compound in perfumery.

THE INVENTION

We have now discovered surprisingly that spiro[5.7]-tridec-1-ene-3-one possesses advantageous odor characters and that, as a result, it can be used for the preparation of perfumes and concentrated perfuming bases and serve to confer, improve or modify the odor of various consumer products such as soaps, liquid and solid detergents, fabric softeners, personal care products such as cosmetics, shampoos, creams, hair treatment product or yet household products and ambient air deodorants.

Spiro[5.7]tridec-1-ene-3-one develops iris-type notes, some aspects of which are reminiscent of 5-ethyl-2-nonanol or of p-tert-amylcyclohexanone [Orivone: IFF; see S. Arctander, Perfume and Flavor Chemicals, sect. 166, Montclair, N.J., USA (1969)]. The spiro-ketone of the invention further possesses a costus, animal and leather aspect, its bottom notes being reminiscent of linseed and coumarin. Having an excellent olfactive strength, spiro-ketone (I) has very good substantivity on linen, particularly on cotton textiles. Linen washed with detergents perfumed by means of spiro-ketone (I) has shown, after drying, a very pleasant powdery and iris odor, which is also very pronounced. They further develop an almost coumarinic sweetness, giving this ingredient a great value from an olfactive point of view, particularly for all kinds of use in functional perfumery.

The proportions in which spiro-ketone (I) can be used to impart the desired odor effects can vary in a wide range of values. As a result of its strength, concentrations of the order of 0.5–1% can, in many cases, be sufficient. Lower concentrations values can be used when perfuming functional or household products, for example in soaps and detergents, wherein concentrations of 0.1% can already produce the desired effects. It goes without saying that these concentration values must not be interpreted in a restricted way, the man in the art knowing by experience that, in all practical uses, the choice of such values depends on the nature of the product that one wishes to perfume as well as on the nature of the coingredients in a given composition. Spiro[5.7]tridec-1-ene-3-one can be used alone but, more generally, it will be employed in admixture with the usual solvents, carriers or excipients as well as with perfuming coingredients of current use. Many examples of such coingredients and adjuvants are given in the prior art [see for example S. Arctander, cited work].

The present invention has also as an object, apart from the method above defined, a perfuming composition as well as perfumed articles containing spiro[5.7]tridec-1-ene-3-one as an active perfuming ingredient.

As indicated above, spiro[5.7]tridec-1-ene-3-one is a known compound which can be obtained according to one of the preparation methods described in the cited documents, for example from cyclooctanecarboxaldehyde by reacting with methyl vinyl ketone, in the presence of p-toluenesulfonique acid. The obtained product was analytically identical to that described in the literature.

The invention is described in a more detailed manner by way of the following application examples.

EXAMPLE 1

A base perfuming composition intended for powder detergents was prepared by admixture of the following ingredients:

| Ingredients | Parts by weight |
|---|---|
| Benzyl acetate | 250 |
| Phenylethyl acetate | 100 |
| Styrallyl acetate | 125 |
| 10%* C9 Aldehyde | 50 |
| 10%* C10 Aldehyde | 50 |
| Allyl amyl glycolate | 50 |
| 10%* Methyl anthranilate | 50 |
| Citronellol | 50 |
| Verdyl acetate | 25 |

-continued

| Ingredients | Parts by weight |
|---|---|
| 10%* Diphenyloxyde | 200 |
| p-tert-Butylcyclohexyl acetate | 250 |
| Madagascar clover oil | 100 |
| Galaxolide 50 MIP[1)] | 200 |
| Galione[2)] | 50 |
| Raw geraniol (Glidden) 465 | 100 |
| Lilial ® [3)] | 100 |
| Linalol | 1000 |
| 10%* Purified menthone | 250 |
| Patchouli oil | 125 |
| Phenylethyl phenylacetate | 50 |
| Brazil Orange essential oil | 125 |
| Amyl salicylate | 100 |
| Benzyl salicylate | 150 |
| Hexyl salicylate | 3500 |
| Terpineol | 2000 |
| Tetrahydromuguol[1)] | 600 |
| Polywood ® [4)] | 50 |
| Synth. Ylang | 50 |
| Coumarin | 100 |
| Total | 9850 |

*in dipropyleneglycol (DIPG)
[1)]origin: International Flavors and Fragrances Inc., USA
[2)]methylionone: origin: Firmenich SA, Geneva, Switzerland
[3)]origin: L. Givaudan, Vernier, Switzerland
[4)]1,7,7,-trimethylbicyclo[4.4.0]decyl acetate: origin: Firmenich SA, Geneva, Switzerland When 15 parts by weight of spiro[5.7]tridec-1-ene-3-one were added to 985 parts by weight of this base composition, a novel composition was obtained which possessed a marked iris and violet-type character. The spiro[5.7]tridec-1-ene-3-one added imparted to the composition a cleanliness odor character whose note pleasantly married the sweetness of the powdery notes of the coumarinic, methylionone type or of the salicylate type.

EXAMPLE 2

A base perfuming composition of the vetyver-type was prepared by admixture of the following ingredients:

| Ingredients | Parts by weight |
|---|---|
| Vetyver Haiti oil | 500 |
| Rhubofix[1)] | 20 |
| Vertofix coeur[2)] | 260 |
| Cedroxyde[3)] | 100 |
| Cedrol | 100 |
| Total | 980 |

[1)]epoxyethyl-methyltricycloundecene: origin: Firmenich SA, Geneva, Switzerland
[2)]origin: International Flavors and Fragrances Inc., USA
[3)]trimethylcyclododecatriene epoxyde: origin: Firmenich SA, Geneva, Switzerland When spiro[5.7]tridec-1-ene-3-one was added in an amount of 2% by weight to the thus prepared perfuming base, the woody-vetyver character of the composition was reinforced, while the compound of the invention also imparted to said composition a very natural character.

What we claim is:

1. A method to confer, improve, enhance or modify the odor properties of a perfuming composition or a perfumed article, which method comprises adding to said composition or article a fragrance effective amount of spiro[5.7]tridec-1-ene-3-one.

2. A perfuming composition containing as an active perfuming ingredient spiro[5.7]tridec-1-ene-3-one in combination with current solvents, carriers or excipients as well as other perfuming ingredients of current use.

3. A perfumed article containing as an active perfuming ingredient spiro[5.7]tridec-1-ene-3-one.

4. A perfumed article according to claim 3 in the form of a soap, a detergent, a fabric softener, a cosmetic preparation, a cream, a shampoo, a hair care product, a household product or an ambient air deodorant.

5. A method to confer, improve, enhance or modify the odor properties of a perfuming composition or a perfumed article, which method comprises adding to a perfuming base or a consumer product spiro[5.7]tridec-1-ene-3-one in an olfactively perceptible amount.

* * * * *